(12) United States Patent
Sinsheimer et al.

(10) Patent No.: US 9,875,821 B2
(45) Date of Patent: Jan. 23, 2018

(54) X-RAY FILTER FOR X-RAY POWDER DIFFRACTION

(71) Applicant: Brookhaven Science Associates, LLC, Upton, NY (US)

(72) Inventors: John Jay Sinsheimer, Farmingville, NY (US); Raymond P. Conley, Naperville, IL (US); Nathalie C. D. Bouet, Wading River, NY (US); Eric Dooryhee, Manorville, NY (US); Sanjit Ghose, Stony Brook, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 0 days.

(21) Appl. No.: 14/955,404

(22) Filed: Dec. 1, 2015

(65) Prior Publication Data

US 2016/0155525 A1 Jun. 2, 2016

Related U.S. Application Data

(60) Provisional application No. 62/085,870, filed on Dec. 1, 2014.

(51) Int. Cl.
*G01N 23/203* (2006.01)
*G21K 1/10* (2006.01)
*G01N 23/20* (2006.01)

(52) U.S. Cl.
CPC .......... *G21K 1/10* (2013.01); *G01N 23/20008* (2013.01)

(58) Field of Classification Search
CPC .... G01N 23/06; G01N 23/203; G01N 23/207; G01N 23/22; G21K 1/10; G21K 1/04; G21K 1/025; G21K 1/067; G21K 1/02; G21K 1/06; G21K 2201/067; G21K 2201/064; A61B 7/4035; A61B 6/482; A61B 6/4042; A61B 6/405; A61B 6/583; A61B 90/39
USPC .... 378/70, 71, 51, 49, 6, 46, 203, 207, 147, 378/156
See application file for complete search history.

(56) References Cited

PUBLICATIONS

Nielsen, S. F., et al., "A conical slit for three-dimensional XRD mapping," J. Synchrotron Rad. (2000) 7, pp. 103-109.
Martins, R. V., et al., "Depth resolved strain and phase mapping of dissimilar friction stir welds using high" Textures and Microstructures (2003), vol. 35, No. 3/4, pp. 145-152.
Bunge, H.J., et al., J. Appl. Cryst. (2003). 36, pp. 1240-1255.
Poulsen, H. F. J. Appl. Cryst. (2012) 45, pp. 1084-1097.
Giessen, B.C., et al., Science (1968) 159, p. 973.

(Continued)

*Primary Examiner* — Don Wong
(74) *Attorney, Agent, or Firm* — Dorene M. Price

(57) ABSTRACT

Technologies are described for apparatus, methods and systems effective for filtering. The filters may comprise a first plate. The first plate may include an x-ray absorbing material and walls defining first slits. The first slits may include arc shaped openings through the first plate. The walls of the first plate may be configured to absorb at least some of first x-rays when the first x-rays are incident on the x-ray absorbing material, and to output second x-rays. The filters may comprise a second plate spaced from the first plate. The second plate may include the x-ray absorbing material and walls defining second slits. The second slits may include arc shaped openings through the second plate. The walls of the second plate may be configured to absorb at least some of second x-rays and to output third x-rays.

20 Claims, 9 Drawing Sheets

(56) References Cited

PUBLICATIONS

Kirshenbaum, K.C., et al., Phys. Chem. Chem. Phys. (2014). 16, p. 9138.
Larson, B.C., et al., Nature. (2002) 415, pp. 887-890.
Wroblewski, T. Nuclear Instruments and Methods in Physics Research, A 428, (1999) pp. 570-582.

X-RAY FILTER FOR X-RAY POWDER DIFFRACTION

CROSS-REFERENCE TO A RELATED APPLICATION

This application claims the benefit under 35 U.S.C. 119(e) of U.S. Provisional Application No. 62/085,870 filed on Dec. 1, 2014 the contents of which are incorporated herein in its entirety.

The present application was made with government support under contract number DE-AC02-98CH10886 and DE-SC0012704 awarded by the U.S. Department of Energy. The United States government has certain rights in the invention(s).

FIELD OF THE INVENTION

This disclosure relates generally to x-ray powder diffraction, a technique used for analyzing and identifying crystalline material.

BACKGROUND

In x-ray powder diffraction, x-rays are directed at a polycrystalline sample and the diffracted x-rays are collected. The diffracted x-rays may form a diffraction pattern produced from coherently scattered x-rays by periodically spaced atoms in the sample, as described by Bragg's law of diffraction. The diffraction pattern may include information about the crystalline structure of the sample. Peaks observed in the diffraction pattern may be analyzed to identity interatomic distances within the sample.

SUMMARY

In some examples, filters are generally described. The filters may comprise a first plate. The first plate may include an x-ray absorbing material and walls defining first slits. The first slits may include arc shaped openings through the first plate. The walls of the first plate may be configured to absorb at least some of first x-rays when the first x-rays are incident on the x-ray absorbing material, and to output second x-rays. The filters may comprise a second plate spaced from the first plate. The second plate may include the x-ray absorbing material and walls defining second slits. The second slits may include arc shaped openings through the second plate. The walls of the second plate may be configured to absorb at least some of second x-rays and to output third x-rays.

In some examples, methods to implement a filter are generally described. The methods may comprise aligning a first plate spaced from a second plate. The first plate may include an x-ray absorbing material and walls defining first slits. The walls of the first plate may be configured to absorb at least some of first x-rays when the first x-rays are incident on the x-ray absorbing material, and to output second x-rays. The second plate may include the x-ray absorbing material and walls defining second slits. The walls of the second plate maybe configured to absorb at least some of second x-rays and to output third x-rays. The methods may comprise positioning the spaced first and second plates a distance from a sample. The first and second plates may be aligned a distance from the sample. The methods may further comprise directing fourth x-rays at the sample. At least some of fourth x-rays may be diffracted by the sample to produce the first x-rays.

In some examples, filter systems are generally described. The filter systems may comprise a first plate. The first plate may include an x-ray absorbing material and walls defining first slits. The first slits may include arc shaped openings through the first plate. The walls of the first plate may be configured to absorb at least some of first x-rays when the first x-rays are incident on the x-ray absorbing material, and to output second x-rays. The systems may comprise a second plate spaced from the first plate. The second plate may include the x-ray absorbing material and walls defining second slits. The second slits may include arc shaped openings through the second plate. The walls of the second plate may be configured to absorb at least some of second x-rays and to output third x-rays. The system may comprise an area detector positioned so as to receive the third x-rays. The system may further comprise an x-ray source configured to direct fourth x-rays at a sample. At least some of fourth x-rays may be diffracted by the sample to produce the first x-rays.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing gad other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

Figure 1:
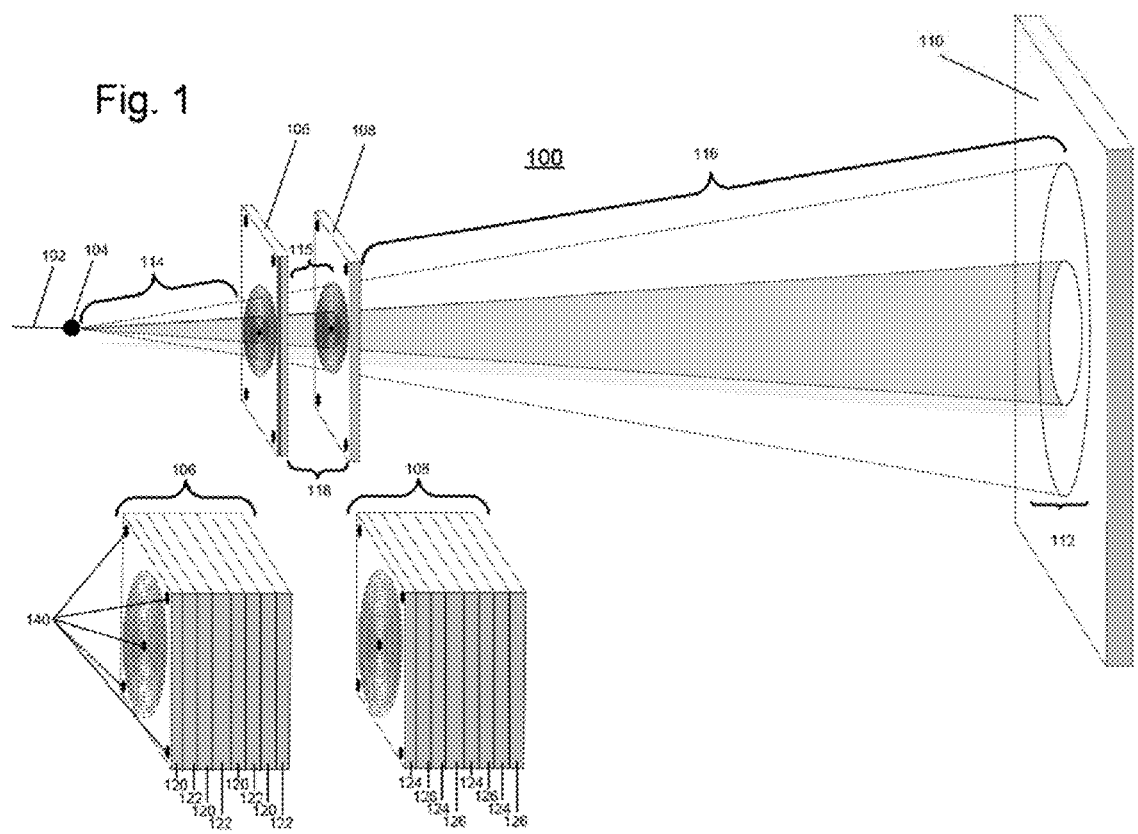
FIG. 1 illustrates an example system for filtering x-rays in x-ray powder diffraction utilizing plates with slits in a spider web design.

all arranged according to at least some embodiments described herein.

DETAILED DESCRIPTION

In the following detailed description, reference is made to the accompanying drawings, which form a part hereof. In the drawings, similar symbol typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

As used herein, any compound, material or substance which is expressly or implicitly disclosed in the specification and/or recited in a claim as belonging to a group or structurally, compositionally and/or functionally related compounds, materials or substances, includes individual representatives of the group and all combinations thereof.

FIG. 1 illustrates an example system 100 for filtering x-rays in x-ray powder diffraction utilizing plates with slits in a spider web design, arranged in accordance with at least some embodiments presented herein. As discussed in more detail below, plates with slits in a spider web design or spider web slits formed by such plates may be utilized to perform filtering of x-rays in x-ray powder diffraction.

System 100 may receive an x-ray beam 102 and a sample 104. System 100 may include a first stack of plates 106, a second stack of plates 108, and an area detector 110. First stack of plates 106 and second stack of plates 108 may be square from a front perspective. First stack of plates 106 and second stack of plates 108 may include walls which define slits or small arc shaped openings through first stack of plates 106 or through second stack of plates 108, respectively. Each slit may have a length associated with a longer are length of the arc shaped opening and a width associated with a shorter radial width of the arc shaped opening. As described in more detail below, when viewed from a front perspective, slits defined by walls of first stack of plates 106 and walls of second stack of plates 108 may appear in a circular, spider web design or pattern. Slits defined by walls of first stack of plates 106 and walls of second stack of plates 108 may extend from about the center of first stack of plates 106 or second stack of plates 108 to the outer edges of first stack of plates 106 or second stack of plates 108.

X-ray beam 102 may be generated by an x-ray source such as a cathode tube or any other x-ray generating technique. X-ray beam 102 may be 1 keV to 120 keV, 30 keV to 120 keV, 30 keV to 100 keV, or 40 keV to 70 keV x-rays (energy range). In an example, x-ray beam 102 may be directed at sample 104. X-ray beam 102 may be diffracted upon incidence with sample 104 forming a diffraction cone 114. Diffraction cone 114 may be filtered upon incidence with first stack of plates 106 and second stack of plates 108 and output filtered diffraction cone 116. A diffraction pattern 112 may be detected by area detector 110 upon incidence from filtered diffraction cone 116.

Sample 104 may be a material to be analyzed. Sample 104 may include multiple materials of which only one material is to be analyzed. The one material to be analyzed may be within a region of interest or a gauge volume of sample 104. Sample 104 may be a composite material such as, for example, a battery encased in steel. A user of system 100 may want to analyze electrolytes within the steel encasing of the battery. X-ray beam 102 may diffract upon incidence with the steel casing of the battery as well as upon incidence with the electrolyte within the steel casing of the battery forming diffraction cone 114. Diffraction pattern 112, detected by area detector 110 upon incidence of diffraction cone 114, may be scattered and a desired diffraction pattern for the electrolyte may not be detected due to the scattering from the diffraction upon incidence with the steel casing. As explained in more detail below, first stack of plates 106 and second stack of plates 108 may block or filter a portion of diffraction cone 114 and segregate a diffraction cone from a gauge volume of sample 104 (filtered diffraction cone 116) to be sent to area detector 110.

First stack of plates 106 and second stack of plates 108 may include stacks of plates arranged together surface to surface. First stack of plates 106 include alternating plates 120 and 122 aligned surface to surface. As described in more detail below, first stack of plates 106 may include a plurality of alternating plates, for example, a total of eight alternating plates 120 and 122. Plates 120 and 122 may include walls which define arc shaped openings or through plate 120 or plate 122. Arc shaped openings or slits in alternating plates 120 and 122 may define stack slits in first stack of plates 106. Arc shaped openings or slits in alternating plates 120 and 122 may align when plates 120 and 122 are aligned surface to surface. Arc shaped openings or slits in alternating plates 120 and 122 may overlap when plates 120 and 122 are aligned surface to surface. As described in more detail below, overlapped arc shaped openings or slits in aligned plates 120 and 122 may define stack slits in stack of plates 106 with an effective arc shaped opening smaller than the arc shaped openings in plate 120 and plate 122.

Second stack of plates 108 may include alternating plates 124 and 126 aligned surface to surface. Second stack of plates 108 may include a plurality of alternating plates, for example, a total of eight alternating plates 124 and 126. Plates 124 and 126 may include walls which define arc shaped openings or slits through plate 124 or plate 126. Arc shaped openings or slits in alternating plates 124 and 126 may define stack slits in second stack of plates 108. Arc shaped openings or slits in alternating plates 124 and 126 may align when plates 124 and 126 are aligned surface to surface. Arc shaped openings or slits in alternating plates 124 and 126 may overlap when plates 124 and 126 are aligned surface to surface. As described in more detail below, overlapped arc shaped openings or slits in aligned plates 124 and 126 may define stack slits in stack of plates 108 with an effective arc shaped opening smaller than the arc shaped openings in plate 124 and plate 126.

Plates 120, 122, 124 and 126 may include an x-ray absorbing material, such as a high electron density material, for example, tungsten, gold, silver, palladium, rhodium, osmium, platinum, tantalum, lead, molybdenum or iridium, or combinations thereof. Plates 120, 122,124 and 126 may each be 50 mm×50 mm×0.25 mm thick. First and second stacks of plates may be 50 mm×50 mm×2 mm thick. Walls of plates 120, 122, 124, and 126 may be micromachined to define arc shaped openings. Walls of plates 120, 122, 124, and 126 may define multiple arc shaped openings. Walls of plates 120, 122, 124, and 126 may define multiple arc shaped openings in specific spider web designs or patterns.

Arc shaped openings in plates 120, 122, 124, and 126 or first and second stacks of plates 106, 108 may be filled with an x-ray transparent material for a given x-ray energy. For example arc shaped openings may be filled with silicon and may be transparent to 60 keV x-rays. Walls of plates 120, 122, 124, and 126 may also define five machined holes 140 respectively; one located through a center of each plate and four located at equivalent distances from each corner of each respective plate. Straight dowels may be placed through holes in plates 120 and 122 to align plates 120 and 122 in first stack of plates 106. Straight dowels may be placed in holes in plates 124 and 126 to align plates 124 and 126 in second stack of plates 108. Straight dowels may be placed in holes in plates 120, 122, 124, and 126 to align first stack of plates 106 with second stack of plates 108.

First stock of plates 106 and second stack of plates 108 may be aligned. Second stack of plates 108 may be arranged together surface to surface with the first stack of plates 106 or may be spaced a distance 118 from first stack of plates 106. When second stack of plates 108 is surface to surface with the first stack of plates 106, the distance may be for clarity, 0 mm. When second stick of plates 108 and first stack of plates 106 are spaced, the distance 118 may be based on a detector size or a function of an energy beam in a detector and may be from about 1 mm to about 50 mm, 5 mm to about 50 mm, or about 20 mm. As described in more detail below, slits in first stack of plates 106 may filter diffraction cone 114 as diffraction cone 114 is incident on first stack of plates 106 and output filtered diffraction cone 115. Slits in second stack of plates 108 may filter filtered diffraction cone 115 as diffraction cone 115 is incident on second stack of plates 108 and output filtered diffraction cone 116.

Figure 2:
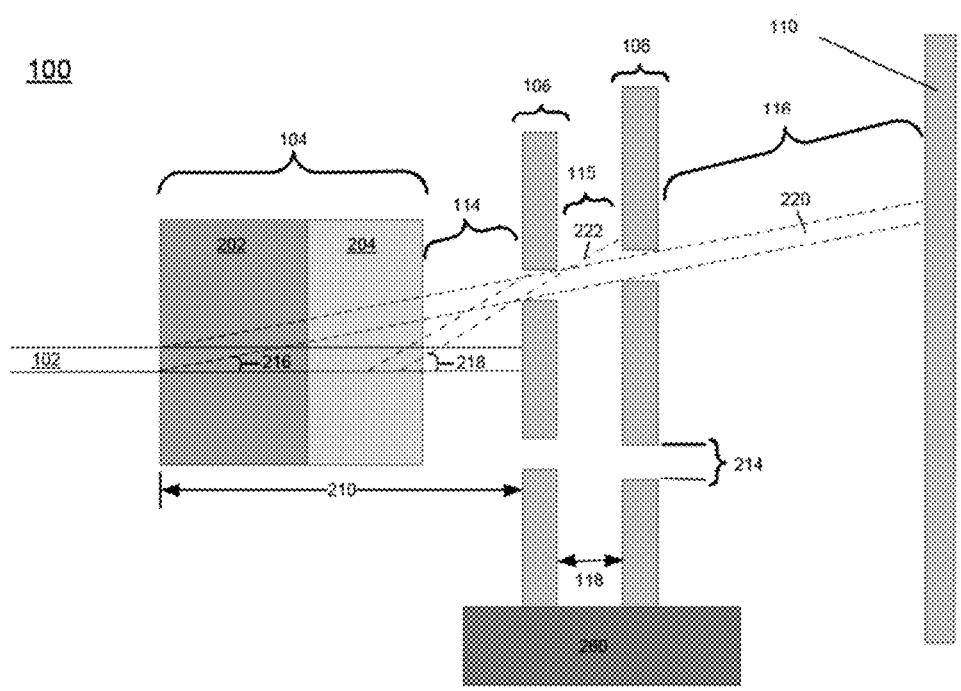
FIG. 2 is a side view for an example system for x-ray powder diffraction utilizing plates with slits in a spider web design.

FIG. 2 is a side view of system 100 for x-ray powder diffraction utilizing plates with slits in a spider web design arranged in accordance with at least some embodiments presented herein. Those components in FIG. 2 that are labeled identically to components of FIG. 1 will not be described again for the purposes of clarity.

Sample 104 may comprise a first material 202 and a second material 204. X-ray beam 102 may diffract than upon incidence with sample 104 including material 202 and material 204. A first portion of x-ray beam 102 may diffract at a first angle 216 upon incidence with material 202. A second portion of x-ray beam 102 may diffract at a second angle 218 when incident upon material 204. A first portion of x-ray beam 102 may diffract upon incident with material 202 resulting in diffracted x-ray beam 220. The second portion of x-ray beam 102 may diffract upon incidence with material 204 resulting in diffracted x-ray beam 222.

First stack of plates 106 may filter diffraction cone 114 as diffraction cone 114 is incident on first stack of plates 106. Diffraction cone 114 may include diffracted x-ray beam 220 and diffracted x-ray beam 222. Slits in first stack of plates 106 may align with diffracted x-ray beam 220, and diffracted x-ray beam 220 may pass through slits in first stack of plates 106. Diffracted x-ray beam 220 may not be absorbed by x-ray absorbing material of first stack of plates 106. Slits in first stack of plates 106 may not align with diffracted x-ray beam 222. Diffracted x-ray beam 222 or a portion of diffracted 223 may be absorbed x-ray absorbing material of first stack of plates 106. First stack of plates 106 may absorb or filter a portion of diffraction cone 114, such as absorbing a portion of diffracted x-ray beam 222, and output filtered diffraction cone 115. Filtered diffraction cone 115 may include diffracted x-ray beam 220 and a portion of diffracted x-ray beam 222 not absorbed by first stack of plates 106. Second stack of plates 108 may be aligned with first stack of plates 106 and filtered diffraction cone 115 may be incident on second stack of plates 108.

Second stack of plates 108 may filter filtered diffraction cone 115. Filtered diffraction cone 115 may include diffracted x-ray beam 220 and a portion of diffracted x-ray beam 222. Slits in second stack of plates 108 may align with diffracted x-ray beam 220. Diffracted x-ray beam 220 may not be absorbed by x-ray absorbing material of second stack of plates 108. Slits in second stack of plates 108 may not align with a portion of diffracted x-ray beam 222. The portion of diffracted x-ray beam 222 may be absorbed by x-ray absorbing material of second stack of plates 108. Second stack of plates 108 may absorb or filer a portion of filtered diffraction cone 115, such as absorbing the portion of diffracted x-ray beam 222, and output filtered diffraction cone 116. Filtered diffraction cone 116 may include diffracted x-ray beam 220.

First stack of plates 106 and second stack of plates 108 may be configured to absorb diffracted x-rays 222 from material 204 of sample 104 while not absorbing diffracted x-rays 220 diffracted from a gauge volume or region of interest of material 202 of sample 104. First stack of plates 106 max be set a distance 210 from the gauge volume or region or interest of sample 104. Distance 210 may be from about 25 mm to about 175 mm. or about 100 mm. Second stack of plates 108 may be spaced a distance 118 from first stack of plates 106. Distance 118 may be from about 5 mm to about 50 mm, or about 20 mm. Diffracted x-ray beam 220 may be front a gauge volume or region of interest over an angular diffraction range of from 2 degrees to 10 degrees. Filtered diffracted x-ray beam 220 may pass through first stack of plates 106 and second stack of plates 108 to area detector 110. First stack of plates 106 and second stack of plates 108 may be mounted and aligned on a holder 260. Holder 260 may include five motors, one motor in each of the x, y, and z direction and two motors for rotation. Holder 260 may align first stack of plates 106 and second stack of plates 108 with sample 104 and detector 110.

Figure 3:
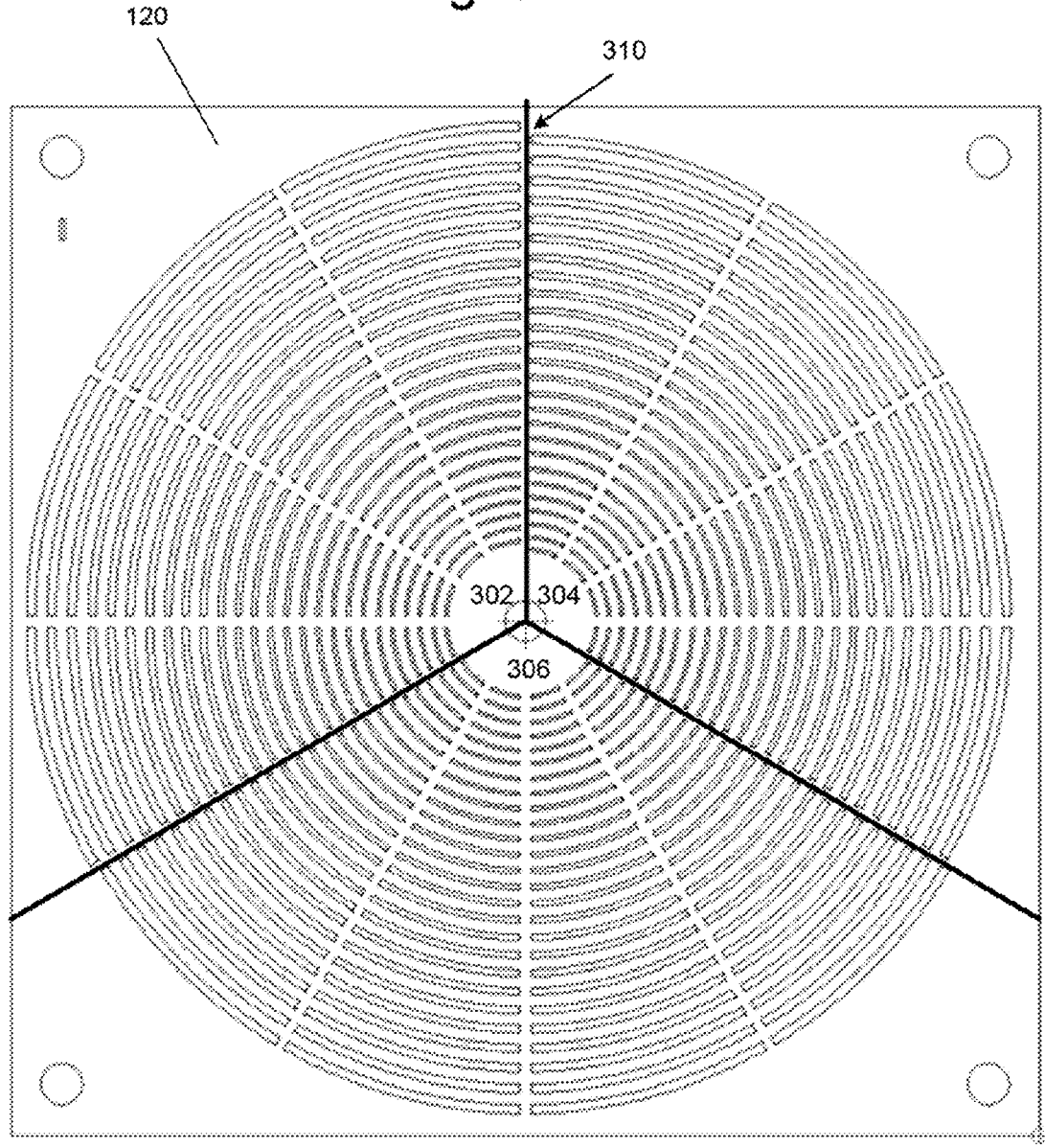
FIG. 3 is a front view of an example of a three section spider web design for slits defined by walls in a plate.

FIG. 3 is a front view of an example of a three section spider web design for slits defined by walls in plate 120, arranged in accordance with at least some embodiments presented herein. A three section spider web design may divide plate 120 into sections 302, 304, and 306. Sections 302, 304, and 306 may each include a set of slits in plate 120 respectively. Sections 302, 304, and 306 may include slits whose lengths define arcs which are offset from one another. For example, as shown at 310, section 302 may include slits in plate 120 which are offset from slits in plate 120 in section 304. Slits in sections 302, 304, and 306 may increase in size (length and width) of the arc shaped opening when viewed radially outward from the center of plate 120. Slits in plate 120, divided into sections 302, 304 and 306 by a three section spider web design, may allow part of a diffraction cone to pass through plate 120 at least one of section 302, 304, or 306. Use of three sections may allow for one third of a diffraction cone to pass through any one of the defined sections.

Figure 4:
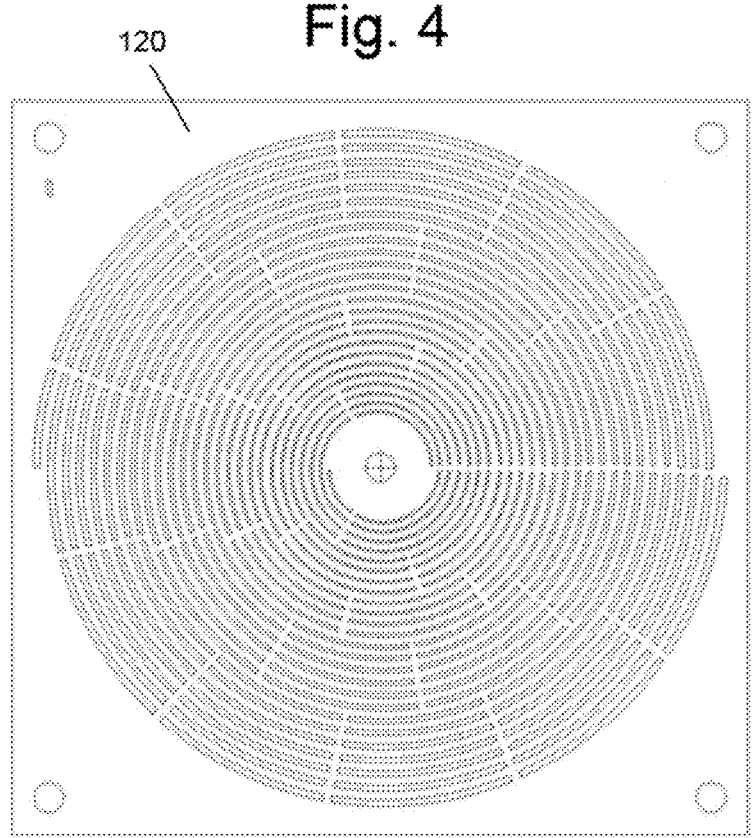
FIG. 4 is a front view of an example of a spider web spiral design for slits defined by walls-in a plate.

FIG. 4 is a front view of an example of a spider web spiral design for slits defined by walls in plate 120, arranged in accordance with at least some embodiments presented herein. As previously described, each slit in plate 120 may have a length associated with a longer arc length of the arc shaped opening and a width associated with a shorter radial width of the arc shaped opening. The spider web spiral design may include slits starting from about the center of plate 120 arcing radially. A placement of the slits may result in a distance from the width of each subsequent slit to the center of plate 120 to increase. The continuous increase in a distance between the width of the slit and the center of plate 120, as well as the increase in distance continuing in subsequent slits may produce a spiral design. Each time the spiral completes 360 degrees around plate 120, the distance between the width of a subsequent slit and the center of plate 120 may increase by a width of a previous slit. Likewise, the width of a slit may continuously increase along the spiral as the distance between the width of the spiral and the center of plate 120 increases, with the exception of the innermost 5-7 rows of the spiral all including slits with a minimum slit width.

Figure 5:
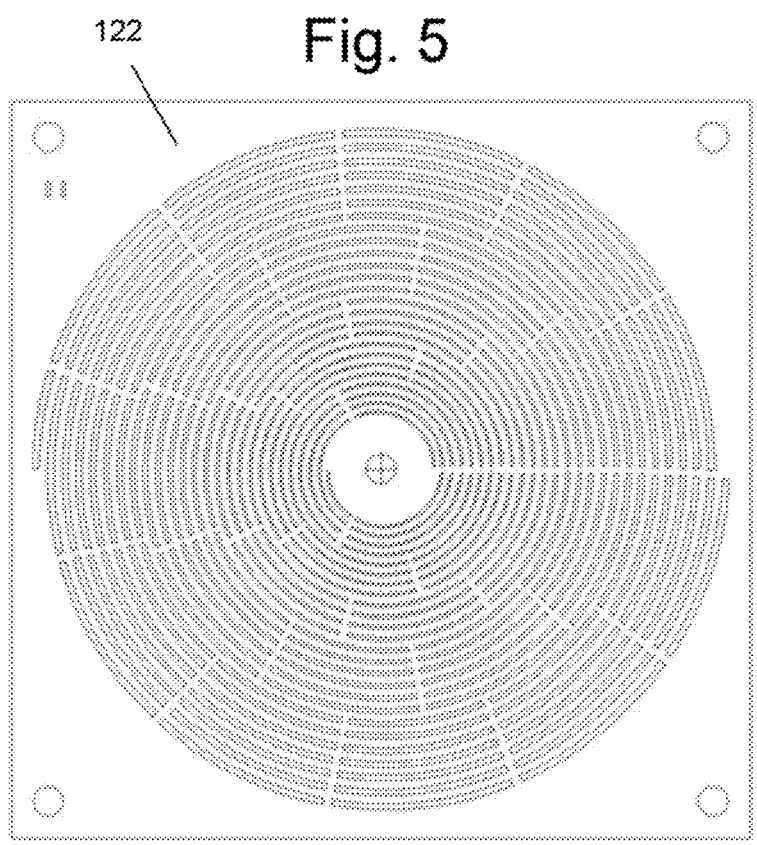
FIG. 5 is a is a front view of an example of a spider web spiral design for slits defined by walls in a plate.

FIG. 5 is a front view of an example of a spider web spiral design for slits defined by walls in plate 122, arranged in accordance with at least some embodiments presented herein. The spider web spiral design may include slits starting from about the center of plate 122 arcing radially. A placement of the slits may result in a distance from the width of each subsequent slit to the center of plate 122 to increase. The continuous increase in a distance between the width of the slit and the center of plate 122, as well as the increase in distance continuing in subsequent slits may produce a spiral design. Each time the spiral completes 360 degrees around plate 122, the distance between the width of a subsequent slit and the center of plate 122 may increase by a width of a previous slit. Likewise, the width of a slit may continuously increase along the spiral as the distance between the width of the spiral and the center of plate 122 increases, with the exception of the innermost 5-7 rows of the spiral all including slits with a minimum slit width. Plate 122 may alternate with plate 120 in a stack of eight alternating plates to form first stack of plates 106. As shown in more detail below, slits in the innermost 5-7 rows of the spiral in plate 120 may overlap slits in innermost 5-7 rows of the spiral in plate 122 to create a smaller effective width.

Figure 6:
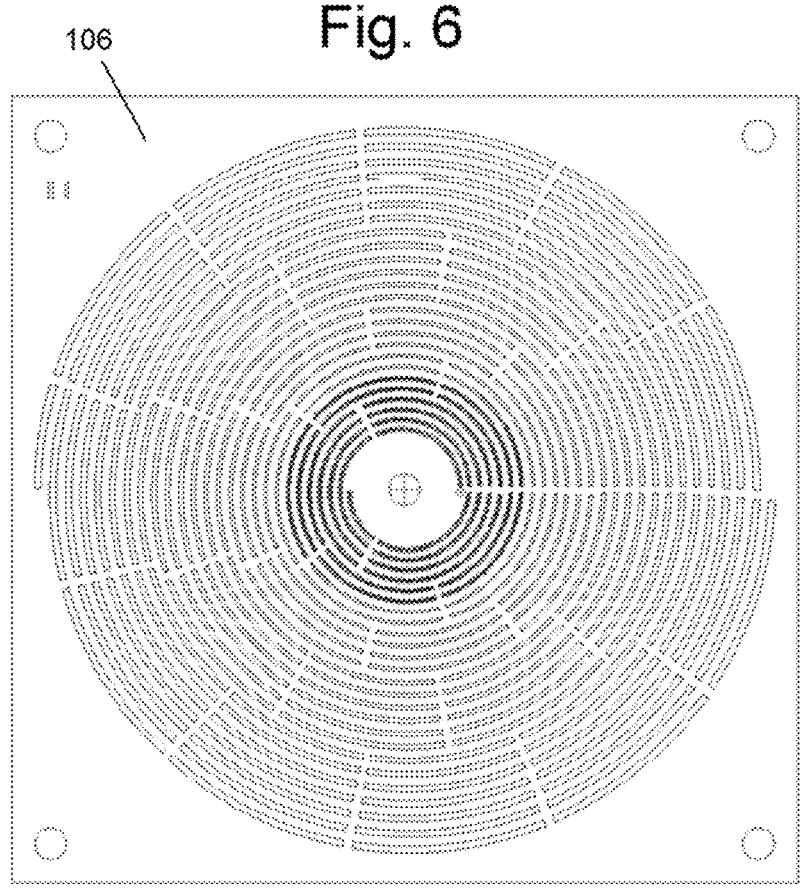
FIG. 6 is a front view of an example of a first plate with slits in a first spider web spiral design overlapping a second plate with slits in a second spider web spiral design.
Figure 7:
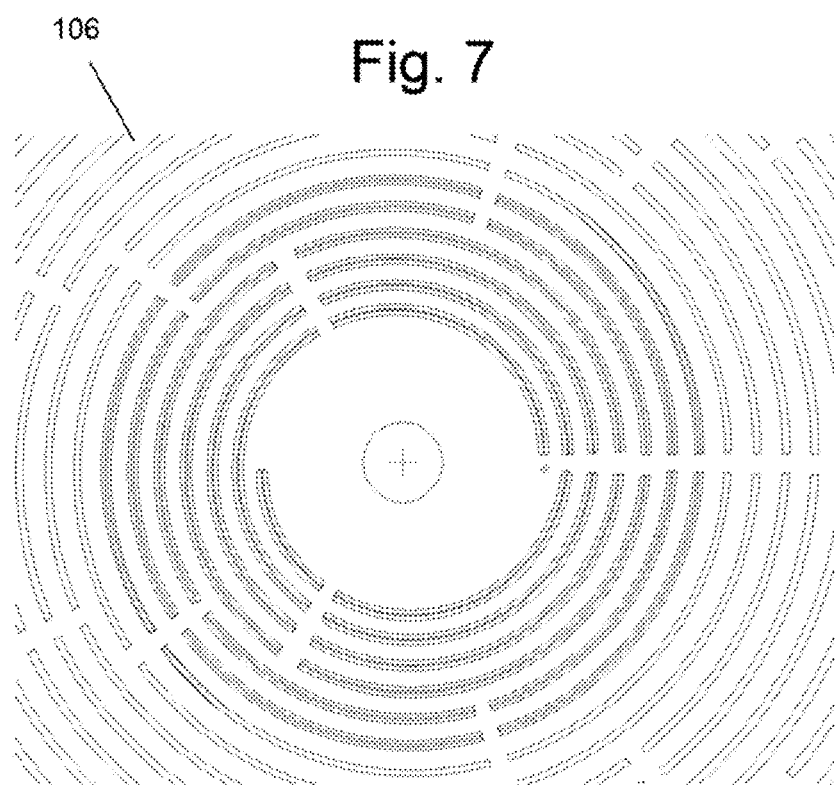
FIG. 7 is a front close-up view of an example of a first plate with slits in a first spider web spiral design overlapping a second plate with slits in a second spider web spiral design.

FIG. 6 is a front view of a first stack of plates 106 with an example of plate 120 with slits in a spider web spiral design overlapping plate 122 with slits in a second spider web spiral design, arranged in accordance with at least some embodiments presented herein. FIG. 7 is a front close-up view of a first stack of plates 106 with an example plate 120 with slits in a spider web spiral design overlapping plate 122 with slits in a second spider web spiral design, arranged in accordance with at least some embodiments presented herein. As shown, in FIG. 6 and FIG. 7 the slits in the innermost 5-7 rows of the spiral in plate 120 may be designed to be staggered from the slits in innermost 5-7 rows of the spiral in plate 122. The slits in the innermost 5-7 rows of the spiral in plate 120 may overlap the slits in the innermost 5-7 rows of spiral in plate 122 when plates 120 and 122 are aligned and stacked in first stack of plates 106. The overlap may create a smaller effective width to the slits in the innermost 5-7 rows of the spiral in first stack of plates 106. For example, it may be desired to obtain innermost slits with widths of about 90 microns, but a laser micromachining process may be limited to producing a slit with a width of about 150 microns. Staggering or offsetting slits with a width of about 150 microns by about 60 microns in first stack of plates 106 may result in an effective slit width of about 90 microns. Effective slit widths for first stack of plates 106 and second stack of plates 108 may range from about 1 micron to about 500 microns.

Figure 8:
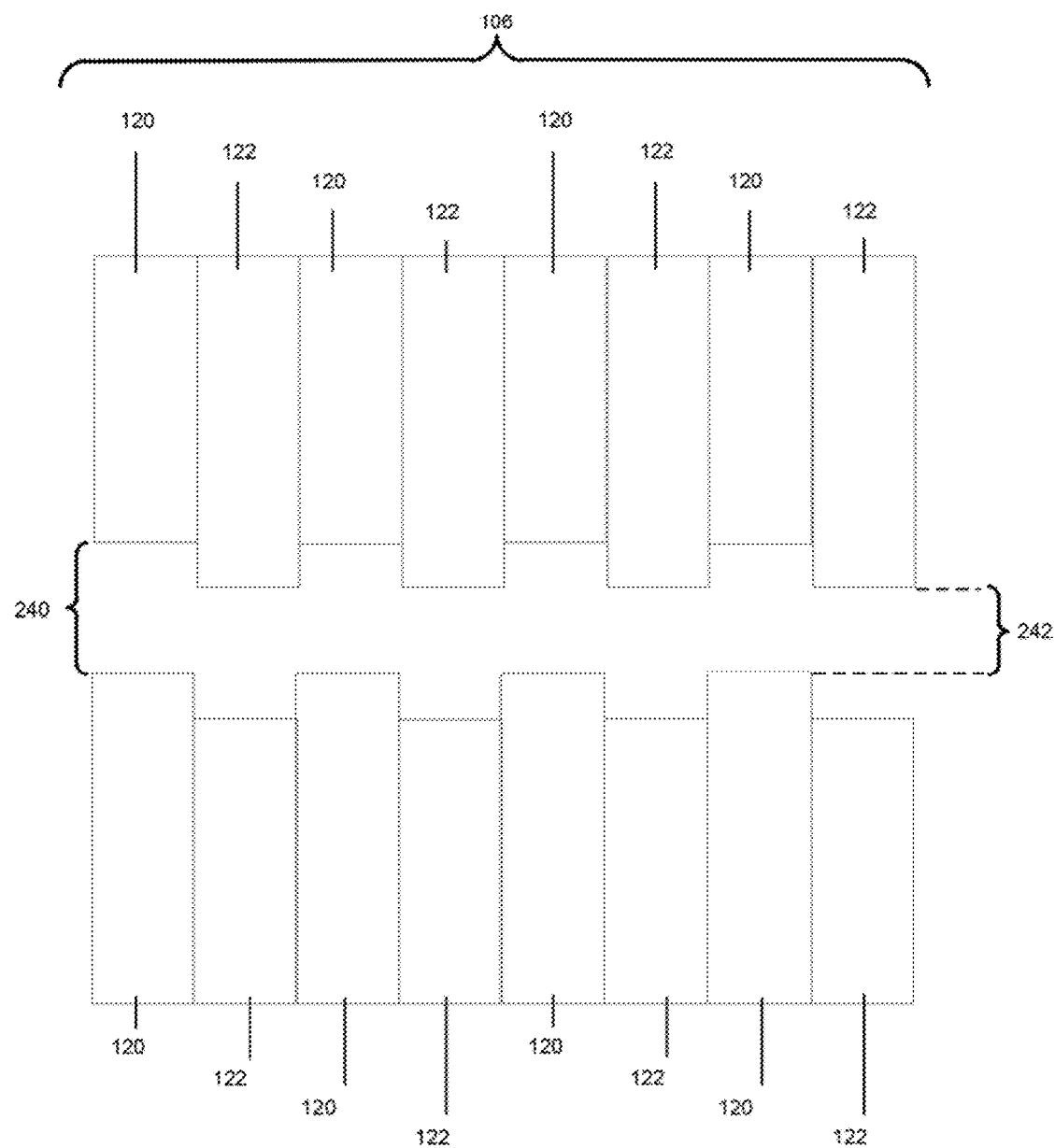
FIG. 8 is a cross-sectional view of a stack of plates showing an effective slit width resulting from staggered slit locations in spider web designs of alternating: plates.

FIG. 8 is a cross-sectional view of first stack of plates 106 showing an effective slit width resulting from staggered sin locations in spider web designs of alternating plates, arranged in accordance with at least some embodiments presented herein. First stack of plates 106 may include eight stacked and aligned alternating plates 120 and 122. The innermost slits defined by wall in plate 120 and the innermost slits defined by walls in plate 122 may be a process limiting width 240. The innermost slits in plate 120 may be designed, such as by a spider web design, to overlap the innermost slits in plate 122 when plates 120 and 122 are aligned and stacked. The overlap in the innermost slits in plate 120 and 122 may create a smaller effective stack slit width 242 for first stack of plates 106.

Figure 9:
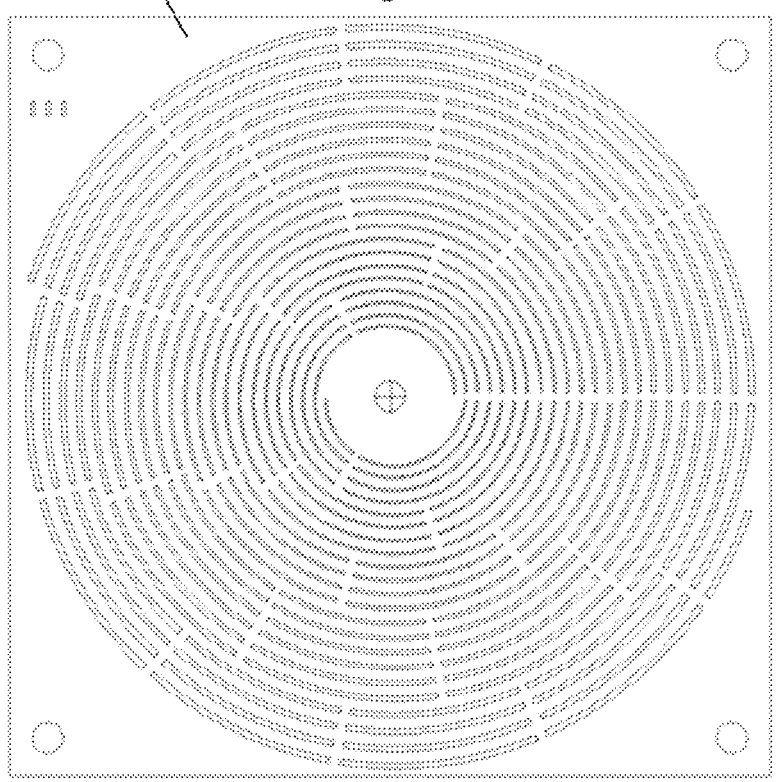
FIG. 9 is a front view of an example of a spider web spiral design for slits defined by walls in a plate.

FIG. 9 is a front view of an example of a spicier web spiral design for slits defined by walls in plate 124, arranged in accordance with at least some embodiments presented herein. The spider web spiral design may include slits starting from about the center of plate 124 arcing radially. A placement of the slits may result in a distance from the width of each slit from the center of plate 124 to increase. The continuous increase in a distance between the width of the slit and the center of plate 124, as well as the increase in distance continuing in subsequent slits may produce a spiral design. Each time the spiral completes 360 degrees around plate 124, the distance between the width of a subsequent slit and the center of plate 124 may increase by a width of a previous slit. The width of a slit may continuously increase along the spiral as the distance between the width of the spiral and the center of plate 124 increases, with the exception of the innermost 5-7 rows of the spiral all including slits with a minimum slit width.

Figure 10:
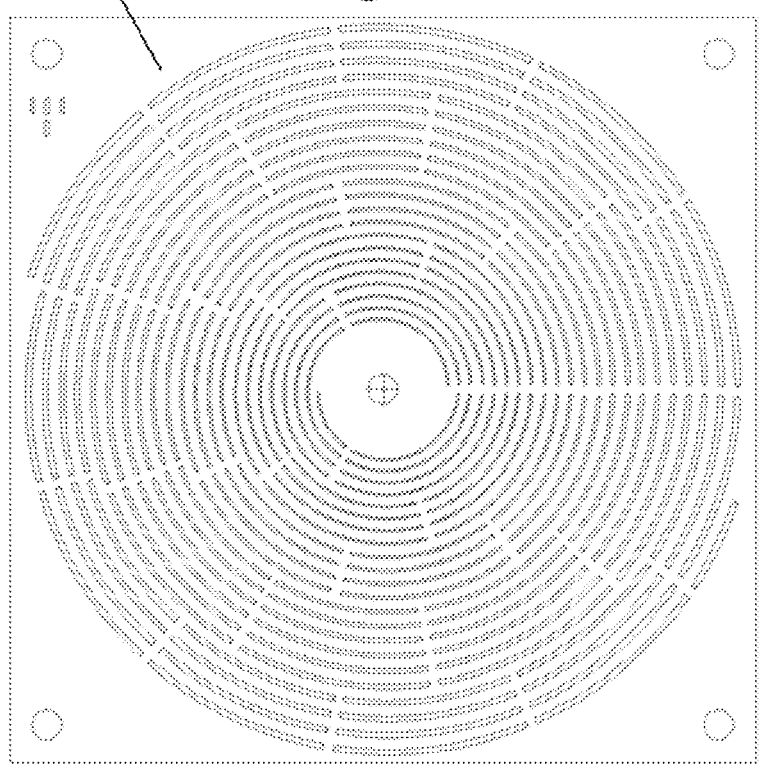
FIG. 10 is a front view of an example of a spider web spiral design for slits in a plates.

FIG. 10 is a front view of an example of a spider web spiral design for slits defined by walls in plate 126, arranged in accordance with at least some embodiments presented herein. The spider web spiral design may include slits starting from about the center of plate 126 arcing radially. A placement of the slits may result in a distance from the width of each slit from the center of plate 126 to increase. The continuous increase in a distance between the width of the slit and the center of plate 126, as well as the increase in distance continuing in subsequent slits may produce a spiral design. Each time the spiral curve completes 360 degrees around plate 126, the distance between the width of a subsequent slit and the center of plate 126 may increase by a width of a previous slit. The width of a slit may continuously increase along the spiral as the distance between the width of the spiral and the center of plate 126 increases, with the exception of the innermost 5-7 rows of the spiral all including slits with a limited minimum slit width. Plate 120 may alternate with plate 124 in a stack of eight alternating plate to form second stack of plates 108. In one example, first stack of plates includes twenty-six rows of slits and second stack of plates 108 includes twenty-two rows of slits.

Figure 11:
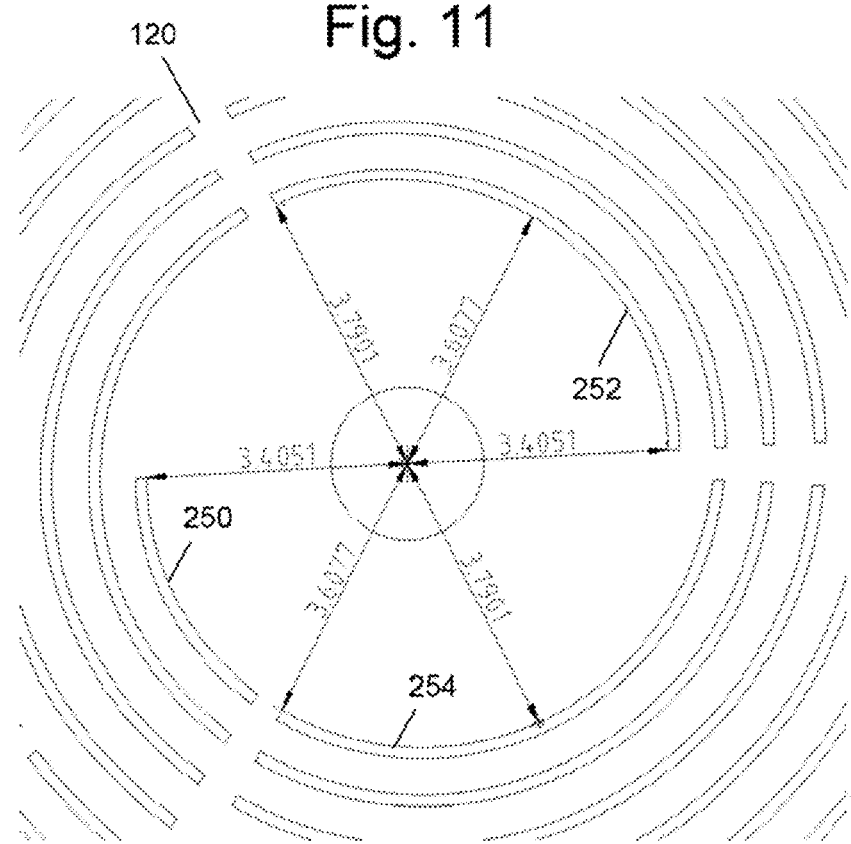
FIG. 11 is a close-up front view of a plate showing distances between slits and the center of a plate.

FIG. 11 is a close-up front view of plate 120 showing distances between slits and the center of plate 120, arranged in accordance with at least some embodiments presented herein. As shown in FIG. 11, slits 250 and 252 are closest to the center of plate 120 at a first end a distance of 3.4051 mm from the center of plate 120. As slits 250 and 252 spiral counterclockwise slits 250 and 252 may increase in distance from the center of plate 120. As shown, slit 252 is a distance of 3.6077 mm from the center of plate 120 at about the midpoint of slit 252, and 3.7901 mm from the center of plate 120 at a second end counterclockwise from the first end. Slit 254 is a subsequent slit to slit 250 and is closest to the center of plate 120 at a first end with a distance of 3.6077 mm. Slit 254 increases in distance from the center of plate 120 to 3.7901 mm at about the midpoint of slit 254. Subsequent slits may continually increase in distance from the center of plate 120 as the subsequent slits spiral counterclockwise.

FIG. 11 also illustrates spiral design symmetry as a first spiral caused by slit 250, slit 254 and subsequent slits and a second spiral caused by slit 252 and subsequent slits display 2-fold rotational symmetry.

Figure 12:
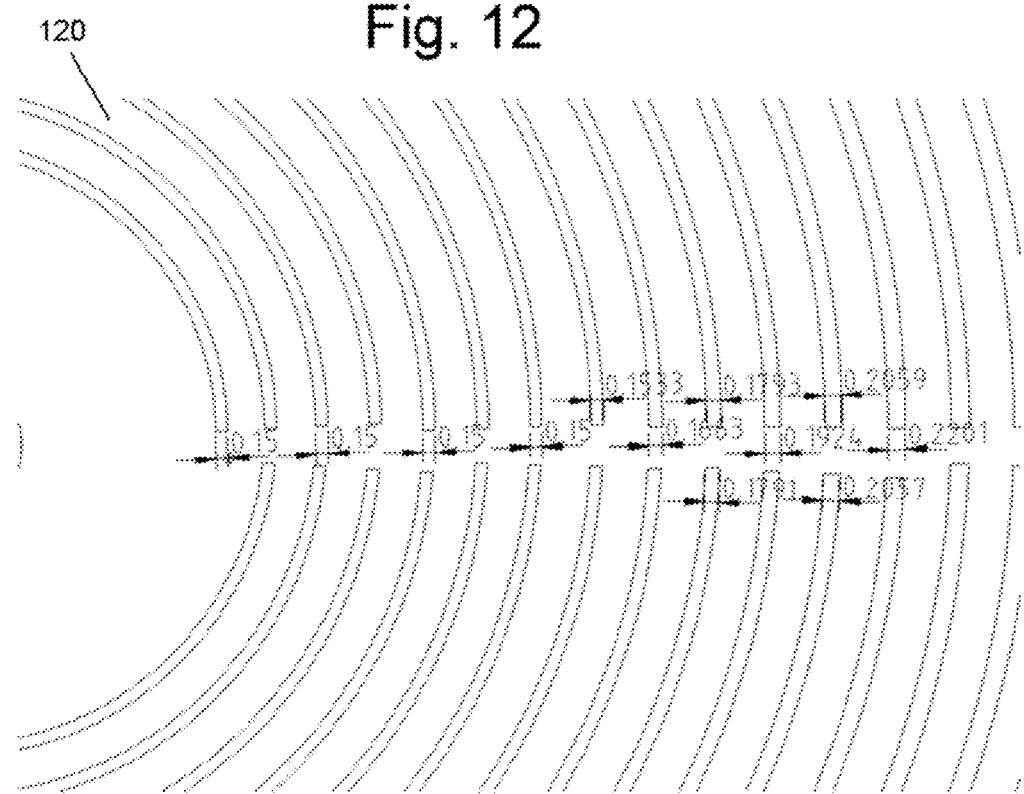
FIG. 12 is a close-up front view of a plate showing slit width in an example spider web spiral design.

FIG. 12 is a close-up front view of plate 120 showing slit width in an example spider web spiral design, arranged in accordance with at least some embodiment presented herein. As shown in FIG. 12, the first 5-7 row of slits closest to the center of plate 120 may have a slit width of 0.15 mm or 150 microns with slit width of subsequent slits increasing with distance from the center of plate 120.

Figure 13:
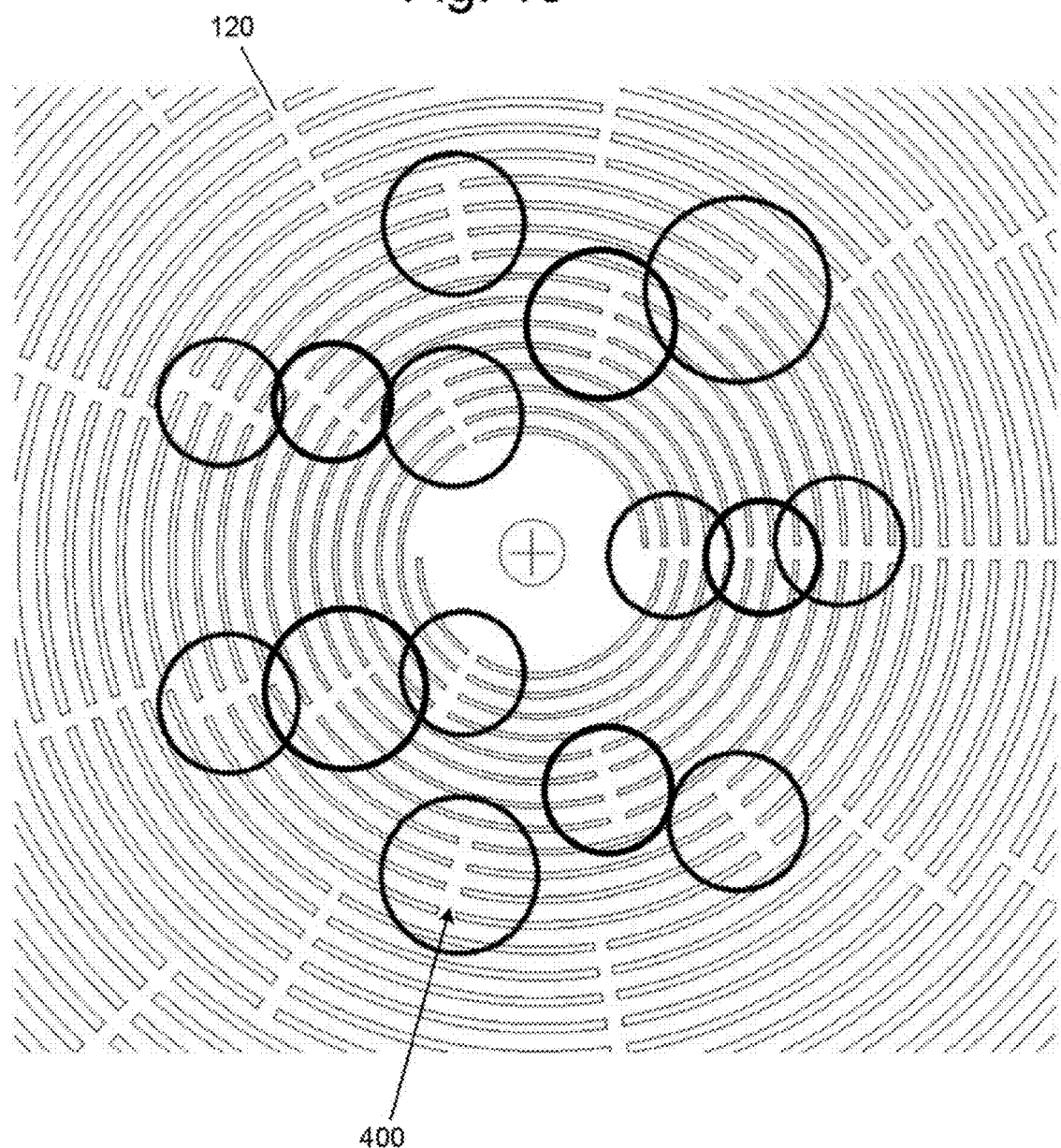
FIG. 13 is a close-up front view of a plate showing a support structure in the plate.

FIG. 13 is a close-up front view of plate 120 showing support structure in plate 120, arranged in accordance with at least some embodiments presented herein. Plate 120 may include walls defining slits in a spiral design. A slit designed as a continuous spiral running counter-clockwise from a center of plate 120 to an outer edge of plate 120 may compromise the integrity and structure of plate 120. Support structures 400 interrupting a continuous spiral may be arranged at specific locations to provide structural integrity to plate 120. Support structures 400 may be designed or patterned to include odd fold symmetry, such as 3-fold or 5-fold symmetry, so that when a support is on one side of plate 120 there is not a support 180 degrees on the other side of plate 120. First stack of plates 106 and second stack of plates 108 may be rotated about a central axis of x-rays directed at first stack of plates 106 so as to detect a full diffraction cone and minimize x-rays absorbed by structural supports 400. An x-ray diffraction detector may record a long exposure, over a set time period or over an integer number of revolutions in a set time period to capture information related to an entire diffraction cone.

Among other possible benefits, a system in accordance with the present disclosure may produce higher resolution diffraction cones making for more accurate analysis. The present disclosure may measure part of a diffraction cone from a particular gauge volume of a sample over an angular range of 2 degrees to 10 degrees and may make the apparatus more versatile because its gauge volume selection is not limited to just a select few angles. The apparatus may also-collect data more rapidly. A system in accordance with the present disclosure may also reduce background diffraction from sample containers, reaction cell windows, or pressure cell windows.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A filter comprising:
a first plate, wherein the first plate includes a center, an x-ray absorbing material and walls defining first slits, wherein the first slits include arc shaped openings through the first plate starting from the center and wherein the arc shaped openings arc radially from the center, form a spiral, and are staggered when viewed radially from respective centers of respective plates, the walls of the first plate configured to absorb at least some of first x-rays when the first x-rays are incident on the x-ray absorbing material and to output second x-rays; and
a second plate spaced from the first plate, wherein the second plate includes a center, the x-ray absorbing material and walls defining second slits, wherein the second slits include arc shaped openings through the second plate starting from the center and wherein the arc shaped openings arc radially from the center, form a spiral, and are staggered when viewed radially from respective centers of respective plates, the walls of the second plate configured to absorb at least some of second x-rays and to output third x-rays.

2. The filter of claim 1, wherein the first and second slits range in width from about 1 micron to about 500 microns.

3. The filter of claim 1, wherein radial distances of the first and second slits continuously increase over angular distances and radial distances between first and second slits continuously increase over angular distances when viewed radially from respective centers of respective plates each time the spiral completes 360 degrees around the first and second plates.

4. The filter of claim 1, wherein the first plate includes an aligned first stack of a plurality of alternating third plates and fourth plates stacked together surface to surface, wherein the third plates include the x-ray absorbing material and
third slits and the fourth slits include the x-ray absorbing material and fourth slits, and the alternating third and fourth slits define the first slits; and
the second plate includes an aligned second stack of a plurality of alternating fifth plates and sixth plates stacked together surface to surface, wherein the fifth plates include the x-ray absorbing material and fifth slits and the sixth plates include the x-ray absorbing material and sixth slits, and the alternating fifth and sixth slits define the second slits.

5. The filter of claim 4, wherein the third and fourth slits are staggered.

6. The filter of claim 1, wherein the first plate and the second plate are aligned with a distance between the first plate and the second plate of about 5 mm to about 50 mm.

7. The filter of claim 1, wherein the first plate and the second plate are aligned with a distance between the first plate and the second plate of about 20 mm.

8. The filter of claim 1, wherein the first and second plates include a high electron density material.

9. The filter of claim 1, wherein the first and second plates include tungsten, gold, silver, palladium, rhodium, osmium, platinum, tantalum, lead, molybdenum, or iridium, or combinations thereof.

10. The filter of claim 1, wherein at least one of the first or second slits are filled with an x-ray transparent material.

11. The filter of claim 10, wherein the transparent material is silicon.

12. A method to implement a filter, the method comprising:
aligning a first plate spaced from a second plate, the first plate including a center, an x-ray absorbing material and walls defining first slits, wherein the first slits include arc shaped openings through the first plate starting from the center and wherein the arc shaped openings arc radially from the center, form a spiral, and are staggered when viewed radially from respective centers of respective plates, the walls of the first plate configured to absorb at least some of first x-rays when the first x-rays are incident on the x-ray absorbing material, and to output second x-rays, the second plate including a center, the x-ray absorbing material and walls defining second slits, wherein the second slits include arc shaped openings through the second plate starting from the center and wherein the arc shaped openings arc radially from the center, form a spiral, and are staggered when viewed radially from respective centers of respective plates, the walls of the second plate configured to absorb at least some of second x-rays and to output third x-rays positioning the aligned first and second plates a distance from a sample; and directing fourth x-rays at the sample, such that at least some of fourth x-rays are diffracted by the sample to produce the first x-rays.

13. A method of claim 12, wherein the first and second slits include arc shaped openings and the first and second slits range in width from about 1 micron to about 500 microns.

14. The method of claim 12, wherein radial distances of the first and second slits continuously increase over angular distances and radial distances between first and second slits continuously increase over angular distances when viewed radially from respective centers of respective plates each time the spiral completes 360 degrees around the first and second plates.

15. The method of claim 12, wherein the first and second plates include tungsten, gold, silver, palladium, rhodium, osmium, platinum, tantalum, lead, molybdenum, or iridium, or combinations thereof.

16. The method of claim 12, wherein the first plate and the second plate are aligned with a distance between the first plate and the second plate of about 5 mm to about 50 mm.

17. The method of claim 12, wherein the first plate and the second plate are aligned with a distance between the first plate and the second plate of about 20 mm.

18. The method of claim 12, wherein the distance from the sample to the first plate is from about 25 mm to about 175 mm.

19. The method of claim 12, wherein the distance from the sample to the first plate is about 100 mm.

20. A filter system comprising:

a first plate, wherein the first plate includes a center, an x-ray absorbing material and walls defining first slits, wherein the first slits include arc shaped openings through the first plate starting from the center and wherein the arc shaped openings arc radially from the center, form a spiral, and are staggered when viewed radially from respective centers of respective plates, the walls of the first plate configured to absorb at least some of first x-rays when the first x-rays are incident on the x-ray absorbing material, and to output second x-rays;

a second plate spaced from the first plate, wherein the second plate includes a center, the x-ray absorbing material and walls defining second slits, wherein the second slits include arc shaped openings through the second plate starting from the center and wherein the arc shaped openings arc radially from the center, form a spiral, and are staggered when viewed radially from respective centers of respective plates, the walls of the second plate configured to absorb at least some of second x-rays and to output third x-rays;

an area detector positioned so as to receive the third x-rays; and an x-ray source configured to direct fourth x-rays at a sample, such that at least some of fourth x-rays are diffracted by the sample to produce the first x-rays.

* * * * *